(12) United States Patent
Burgkart

(10) Patent No.: US 8,131,343 B2
(45) Date of Patent: Mar. 6, 2012

(54) IMPLANT LOCATION POSITIONING SYSTEM

(76) Inventor: Rainer Burgkart, München (DE)

( * ) Notice: Subject to any disclaimer, the term of this patent is extended or adjusted under 35 U.S.C. 154(b) by 487 days.

(21) Appl. No.: 12/224,232

(22) PCT Filed: Feb. 21, 2007

(86) PCT No.: PCT/DE2007/000321
§ 371 (c)(1),
(2), (4) Date: Sep. 12, 2008

(87) PCT Pub. No.: WO2007/095918
PCT Pub. Date: Aug. 30, 2007

(65) Prior Publication Data
US 2009/0054762 A1 Feb. 26, 2009

(30) Foreign Application Priority Data
Feb. 21, 2006 (DE) .......................... 10 2006 008 397

(51) Int. Cl.
*A61B 5/00* (2006.01)
(52) U.S. Cl. ........ 600/424; 600/425; 600/587; 606/130; 623/16.11; 623/914; 128/920
(58) Field of Classification Search .................. 600/407, 600/424, 425, 426, 587; 606/130; 623/16, 623/11, 914; 128/920
See application file for complete search history.

(56) References Cited

U.S. PATENT DOCUMENTS

| | | |
|---|---|---|
| 6,205,411 B1 | 3/2001 | DiGioia et al. |
| 6,226,548 B1 | 5/2001 | Foley et al. |
| 6,470,207 B1 | 10/2002 | Simon et al. |
| 6,503,249 B1 | 1/2003 | Krause |
| 6,535,756 B1 | 3/2003 | Simon et al. |
| 6,697,664 B2 | 2/2004 | Kienzle, III et al. |

(Continued)

FOREIGN PATENT DOCUMENTS

FR 2 721 195 12/1995
(Continued)

OTHER PUBLICATIONS

International Search Report for PCT/DE2007/000321 dated Jul. 26, 2007.
(Continued)

*Primary Examiner* — Brian Casler
*Assistant Examiner* — Amanda Lauritzen
(74) *Attorney, Agent, or Firm* — McCracken & Frank LLC

(57) ABSTRACT

The invention relates to an implant layer positioning system comprising a device that can be fixed to a bone section and is used to plan the positioning of implants in order to enable corrective operations to be performed on the bone with optimum bone contact. Said device reproduces the geometry of at least one section of the implant and can be freely oriented by the operator towards accessible parts of the bone. The inventive system also comprises a control unit which virtually evaluates the relevant implant parts, on the basis of the navigation data of the tracked device and the data input of the planned corrective operation, in the form of three-dimensional geometry bodies in fluoroscopy sketches or other referenced image or geometry data. Once the planned proceedings have been inputted, the control unit of the navigation system can virtually merge the corresponding position of all implant parts with the referenced image or geometry data of the patient in a three-dimensional manner by means of corresponding computational algorithms, and once the device has been oriented, the control unit can store the position of said device with all related dependent positions of the implant parts planned at the same time, and all of the planning information can be made available for use with navigated tools.

20 Claims, 2 Drawing Sheets

U.S. PATENT DOCUMENTS

| | | | |
|---|---|---|---|
| 6,747,646 | B2 | 6/2004 | Gueziec et al. |
| 6,752,080 | B2 | 6/2004 | Fukui |
| 7,318,827 | B2 | 1/2008 | Leitner et al. |
| 2005/0234465 | A1* | 10/2005 | McCombs et al. ............... 606/88 |

FOREIGN PATENT DOCUMENTS

| | | |
|---|---|---|
| GB | 2 052 068 | 1/1981 |

OTHER PUBLICATIONS

Tso C. Y. et al: "A Surgical Planning and Guidance System for High Tibial Osteotomies", *Lecture Notes in Computer Science*, Springer Verlag, Berlin, DE, vol. 1496, 1998, pp. 39-50.

Burgkart, R. et al., "Fluoroskopie-basierte 3D-Navigation am proximalen Femur", Computer Assisted Orthopedic Surgery, Fortbildung Orthopadie 6, Steinkopff Darmstadt 2002, pp. 39-43. (Machine translation is currently best available for this reference.).

Burgkart, R. et al., "Fluoroscopy-based 3D navigation of complex correction osteotomies at the proximal femur", Orthopade, Nov. 2005, vol. 34, No. 11, pp. 1137-1143 (abstract only retrieved from the Internet:<http://www.ncbi.nlm.nih.gov/pubmed/16136338 [retrieved on May 13, 2011], 1 page).

Gottschling, H. et al., "Intraoperative, fluoroscopy-based planning for complex osteotomies of the proximal femur", Int. J. Medical Robotics and Computer Assisted Surgery, 2005 John Wiley & Sons, Ltd., vol. 1, No. 3, pp. 67-73.

Grutzner, P.A. et al., "Computer-assisted LISS plate osteosynthesis of proximal tibia fractures: feasibility study and first clinical results", Computer Aided Surgery, May 2005, vol. 10, No. 3, pp. 141-149 (abstract only retrieved from the Internet:<http://www.ncbi.nlm.nih.gov/pubmed/16321911 [retrieved on May 12, 2011], 1 page).

Hofstetter, R. et al., "Computer-assisted fluoroscopy-based reduction of femoral fractures and antetorsion correction", Computer Aided Surgery, 2000, vol. 5, No. 5, pp. 311-325 (abstract only retrieved from the Internet: <http://www.ncbi.nlm.nih.gov/pubmed/11169877> [retrieved on May 12, 2011], 1 page).

Hofstetter, R. et al., "Fluoroscopy Based Surgical Navigation—Concept and Clinical Applications", CAR '97, Computer Assisted Radiology and Surgery, Proceedings of the 11th International Symposium and Exhibition, Berlin, Jun. 25-28, 1997, Elsevier Science B.V., 1997, pp. 956-960.

Germano, I.M., "The NeuroStation System for Image-Guided, Frameless Stereotaxy", Neurosurgery, vol. 37, No. 2, Aug. 1995, pp. 348-350.

Lemieux, L. et al, "A patient-to-computed-tomography image registration method based on digitally reconstructed radiographs", Medical Physics, vol. 21, No. 11, 1994, pp. 1749-1760 (abstract only retrieved from the Internet:<http://online.medphys.org/resource/1/mphya6/v21/i11/p1749_s1?isAuthorized=no> [retrieved on Mar. 23, 2011], 1 page).

Muller, M.E., "Intertrochanteric Osteotomy: Indication, Preoperative Planning, Technique", The Intertrochanteric Osteotomy, Springer Verlag, Berlin, 1984, pp. 25-66.

Reinhardt, H.F., "Interactive sonar-operated device for stereotactic and open surgery", Proceedings of the Xth Meeting of the World Society for Stereotactic and Functional Neurosurgery, Maebashi, Japan, Oct. 1989, Stereotact Funct Neurosurg, vols. 54-55, 1990, pp. 393-397 (abstract only retrieved from the Internet: <http://www.ncbi.nlm.nih.gov/pubmed/2080355> [retrieved on May 12, 2011], 1 page).

Tang, T.S.Y., "Calibration and Point-Based Registration of Fluoroscopic Images", thesis submitted to the Department of Computing and Information Sicence, Queen's University, Kingston, Ontario, Canada, Jan. 1999, pp. i-101.

* cited by examiner

STATE OF THE ART

IMPLANT LOCATION POSITIONING SYSTEM

BACKGROUND

The introduction of osteosynthesis material or implants for secure attachment of two bone fragments to one another—independently of whether they occurred as a result of a traumatic fracture or were caused iatrogenically by targeted intraoperative separation of a bone (osteotomy)—is a frequent task in accident surgery and orthopedics.

This task represents a special technical challenge for the operator. For example, in the not infrequently necessary surgical correction of incorrect positioning of bones, an iatrogenic separation of the bone with the removal of a correcting wedge is usually necessary. Depending on the procedure, in the case of many osteosynthesis implants (for example angle plate for the upper thigh bone near the hip joint), the anchoring of an implant must be prepared ahead of time before separation of the bone in the bone that will later be a fragment, using a bone blade chisel [Müller 1984, Burgkart 2005]. As long as the bone is intact and as a result of this can be worked on with a chisel and striking tools (the subsequent fragment would be too fragile), the proximal implant anchoring must already be prepared, whereby the operator can predict the later new positioning of the bone fragment complex formed first—previously only with the ability of his spatial imagination—and from that he has to derive the operative procedure.

In other words, in order to correct the faulty position, the bone must be sawed all the way through and be put together again. Before the joining together, a wedge-shaped piece must be removed by means of another saw cut. Then the two parts must be rejoined together while keeping the cut surfaces held together and pressed together, to the extent possible, over the entire surface. For this purpose an angle-shaped implant is used with a long and short lateral side. The short lateral side is hammered into the first bone section (joint head) and the long lateral side is screwed into the second bone section.

In order to be able to hammer the short lateral side into the first bone section, previously a hole with a specific depth, direction and cross-section must be prepared in the particular bone section, with a chisel.

However, in order to hammer in this hole, it is necessary that the bone not yet be separated, because otherwise the first bone section would deviate during the procedure with the chisel since it cannot be held in a fixed manner yet, but is only surrounded by muscle and fatty tissue, which does not provide any hold when the chisel is struck into the bone.

Thus, when viewing the now partly freed bone, the operator must imagine where and in what direction the hole is to be hammered in. For this purpose, the operator must develop a high degree of spatial imagination, so that the hole is produced in such a way that after the separation of the bone and the correction it is in the exactly correct location to be able to accept the implant in the correct position.

It is understandable that these circumstances frequently lead to sub-optimal implant positions, so that either an attempt is made to "compensate" for it by a slight correction—as planned and needed—and/or there is an increased risk of delayed bone healing and loosening of the implant and thus the necessity of repeated surgery(ies).

The exact performance of such an operation is very difficult technically and so far depended greatly—more so than in other procedures—on the experience and manual skill and ability of imagination of the operator. Therefore, there is an urgent need for a technique that simplifies these surgical steps, supports them, and allows them to be better planned.

The first modern approaches to solving this problem consist in the use of computer-assisted navigation methods. Hereby, as a rule, a navigation system (computer-assisted control unit connected to a navigation camera) is used, a reference unit that is attached to the patient as well as calibrated surgical tools. The reference unit and the surgical tools are hereby provided with active or passive markers and in this way can be detected with regard to their spatial position and direction by the navigation camera, whereby these data are then transmitted to the control unit. In this way tools that are moved by hand can be tracked and, when referenced imaged data are available, the tools can, for example, be virtually merged into the image data corresponding to their instantaneous position and thus help the operator during the procedure, and at the same time make various virtual plans possible, for example as described in U.S. Pat. No. 6,226,548 No. 6,747,646; No. 6,752,080 No. 6,697,664; No. 6,535,756; No. 6,470,207; No. 6,205,411; see also the literature references below, which are also included in the present application as state of the art.

Burgkart R, Doter M, Roth M, Schweikard A, Gradinger R: Fluoroscopy-based 3D-navigation at the proximal femur. In: Imhoff A (ed) Computer Assisted Orthopedic Surgery—Fortbildung Orthopädie 6. Steinkopff, Darmstadt 2002, pp. 39-43.

Burgkart R, Gottschling H, Roth M, Gradinger R, Schweikard A.: Fluoroscopy-based 3D navigation of complex corrective osteotomies on the proximal femur. Orthopäde. 2005 November; 34(11): 1137-43.

Foley, et al., Image-guided Intraoperative Spinal Localization, Intraoperative Neuroprotection: Monitoring, Part Three, 1996, pp. 325-340.

Gottschling, H., Roth, M., Schweikard, A., Burgkart, R.: Intraoperative, Fluoroscopy-based planning for complex osteotomies of the proximal femur. International Journal of Medical Robotics and Computer Assisted Surgery 2005 September; Vol. 1(3): 67-73.

Früitzner PA, Suhm N. Computer-assisted LISS plate osteosynthesis of proximal tibia fractures: Feasibility study and first clinical results. Computer Aided Surgery 2005; 10(3): 141-149.

Hofstetter R, Slomczykowski M, Krettek C, Koppen G, Sati M, Nolte LP.: Computer-assisted fluoroscopy-based reduction of femoral fractures and antetorsion correction. Comput Aided Surg. 2000; 5(5): 311-25.

Hofstetter, R., et al., Fluoroscopy-based surgical navigation—concept and clinical applications, computer Aided Radiology and Surgery, Elsevier Scient B. V., pp. 956-960 (1997).

Kelly, The NeuroStation system for image-guided, frameless stereotaxy, neurosurgery, Vol. 37, No. 2, August 1995, pp. 348-350.

Lemieux, L. et al., A patient-to-computed-tomography image registration method based on digitally reconstructed radiographs, Medical Physics, Vol. 21, No. 11, pp. 1749-1760 (1994).

Müller M. E.: Intertrochanteric Osteotomy: Indication, preoperative planning, technique. In: Schatzker J. (ed): The intertrochanteric osteotomy. Springer Verlag, Berlin 1984, p. 25-66.

Pfeiffer S.: Medical simulation systems—navigation and robotics in orthopedic surgery, Institute for Computer Design and Error Tolerance (IRF), University of Karlsruhe (TH), 2004. p. 24.

Reinhardt, et al., Interactive sonar-operated device for stereotactic and open surgery, Proceedings of the Xth Meeting of the World Society for Stereotactic and Functional Neurosurgery, Maebashi, Japan, October 1989, pp. 393-397.

Tang, Thomas S. Y., Calibration and point-based registration of fluoroscopic images, Thesis submitted to Dept. of Computing and Information Science, Queen's University, Kingston, Ontario, Canada (1999).

Besides the most frequently used optical navigation cameras, the recognition of position and orientation of patient and tools or implants can also be achieved by ultrasound-based, electromagnetic, or other detection methods (for example, U.S. Pat. No. 6,503,249). However, the basic principles outlined above are identical.

Regarding the problem outlined above regarding an exact planning for the spatially-correct positioning of implants, now we have the first attempts to merge the implants—analogously to the tools outlined above—virtually by visualization of simplified geometric bodies of these implants with referenced image data (for example intraoperatively produced x-ray images) and thus—in bone areas that are difficult to see—make it more clear for improved alignment of the implant by the operator [Grüzner PA. et al. 2004+2005, Hofstetter et al. 2000]. A decisive problem of this virtual implant position planning is, however, that although the implants, which mostly have a rectangular, plate-like cross section, can be aligned virtually in the computer in the longitudinal direction along the projected bone surfaces of the intraoperatively produced two-dimensional x-ray images, this however, does not ensure that the entire implant support surface comes into contact with the bone surface over the entire surface area. In reality, using this procedure, mostly only a bone contact with insufficient stability can be preplanned, since the implants are mostly planned on a tilt, and thus contact is only obtained along an edge, that is, only along a line, and not, as required, as a full-surface contact.

Therefore it is the task of the invention to provide a technique with which the problems described above can be solved better, so that the implants, to a great extent, have a full-surface contact to the bone after implantation.

SUMMARY

This task is solved with an implant location positioning system according to claim 1, which has the following:
- a trackable device having a bone contact surface that matches a bone contact surface of the first section of the implant, wherein the device can be located and moved on the accessible bone surface to maximize contact surface with the accessible bone surface, and
- a navigation system for tracking the position of the device relative to the position of the bone that includes a computer-aided control unit that is adapted to calculate and virtually merge in a spatially correct manner implant parts with image or geometric data of the bone, wherein the calculation is based on navigational data of the trackable device and on data input of planned corrective measures, wherein the computer-aided control unit is further adapted to, after data input of the planned corrective measures, with the aid of corresponding calculation algorithms, and as a function of the position of the device on the accessible bone surface, virtually merge the corresponding position of the second section of the implant with the referenced image or geometric data of the bone, wherein the computer aided control unit is still further adapted to calculate the position of the second section of the implant geometrically offset to take into account a correction equal to the geometry of the planned geometric shift.

The present invention also uses the conventional navigation system as basis, but for the planning a virtual implant is not shifted virtually in the control unit, but rather a specially tracked device is. This device carries in it all the geometric characteristics of the original implant necessary for the planning as characteristics, and is shifted on the real bone in the surgical field.

The preparatory steps before use of the device according to the invention described here are performed according to the known procedures of conventional commercial navigation systems.

For this purpose, after setting up the navigation system and aligning the camera unit to the surgical field, stable fixation of a reference tracker is performed on the bone to be operated on of the patient. Finally, intraoperative image data (for example in the form of fluoroscopy recordings with a tracked, calibrated x-ray C-arc) or image-free geometric data of the patient are produced or image data obtained before surgery (for example CT scans) are referenced with the aid of various known matching methods with the actual position of the patient, which is available to the person skilled in the art from the literature cited above. In this way, patient data, that is bone data, are available in the computer-assisted navigation control unit, on which the operator can plan his procedure. For example, if an x-ray C-arc is used, then mostly 2 x-ray recordings of the surgical treatment area are made from two different directions so that, in this way, for example, the exact spatial position of an anatomical region or of a navigated tool can be calculated inversely with known calculation methods [Brack 1998, among others] and can be virtually imaged in a spatially correct manner within the patient coordinate system and thus also calculated back in the x-ray images.

The invention will now be explained in more detail with the aid of FIGS. 1 to 6.

DETAILED DESCRIPTION

Figure 1:
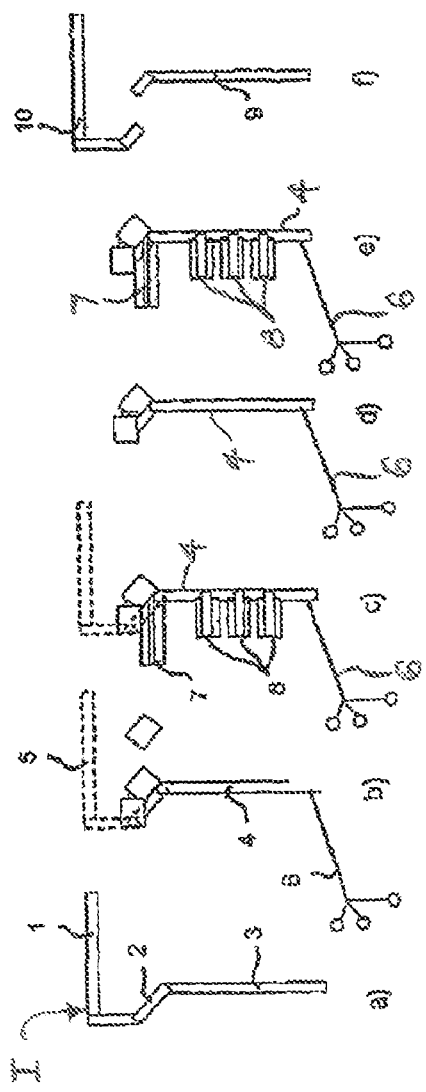
FIGS. 1a-1f are schematic view of implants according to various aspects of the invention.

In FIG. 1a, in the side view a typical implant I to be used is shown: a "right angle plate", using a schematic representation. Hereby this consists of a blade part 1, which is driven into the bone, a right-angle bend 2 (because of the anatomy—trochanter major) and a plate-part 3, which must be flush with the bone surface. The simplest form of the device is shown in FIG. 1b for the sake of understanding the device according to the invention (solid part without dotted line) and shows that the device 4 consists only of the plate part, which has a form and dimensions identical to the original plate part 3, and, for example, of a small part of the right angle bend 2 (in any case only parts that lie outside the bone). Such implants I are frequently rounded at the bone contact surface in order to correspond to the bone geometry better, which is mostly round. The device 4 always has an identical geometry. For the sake of understanding, part of the entire implant I that is not contained in the device 4 is shown with a dotted line 5. A tracker 6 is attached to the device 4. In FIG. 1*c* the same device 4 is shown expanded by one possible functionality such as guides 7 (at least 2 or more) for the boring of parallel Kirschner wires at the level of the osteotomy plane to be planned or for example fixed bore sleeves (8) for precise guiding of drills in order to prepare the holes for the screws. The Kirschner wires can serve, for example, directly as a guide for the saw blade placed on tangentially, or, with the aid of the Kirschner wires a special saw blade caliber is fixed exactly on the bone and then the sawing is done above that.

FIGS. 1*d* and *e* show the corresponding device 4 without the part 5 of the whole implant shown with the dotted line that is not contained in it.

FIG. 1*f* shows the implant I as it is used in the further procedure as at least two virtual bodies 9 and 10. Hereby, in this example of the application it consists of two parts: a part 9 that corresponds to the plate 3 and a part that is supposed to visualize the right angle bend 2, which corresponds geometrically to device 4, and a part 10 that represents the rest of the implant and especially comprises the entire blade section 1. As a result of the fact that the virtual implant is divided into its two essential parts 9 and 10, each one can, itself, be merged correctly on the x-ray images, although the planned correction surgery, with its corresponding change of the bone geometry, has not yet been performed. Otherwise, it would be complicated to simulate on the x-ray plane the later correction, for example by a wedge-shaped "removal" of x-ray image parts with new positioning of the rest of the x-ray parts.

Figure 2:
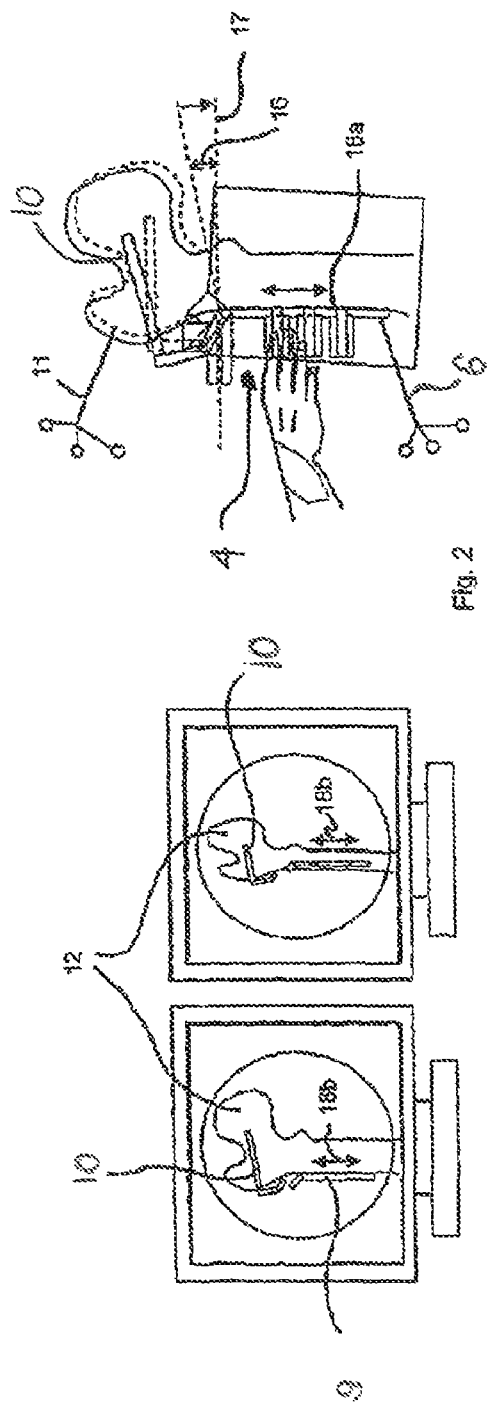
FIG. 2 is a schematic view of additional aspects of the invention.
Figure 3:
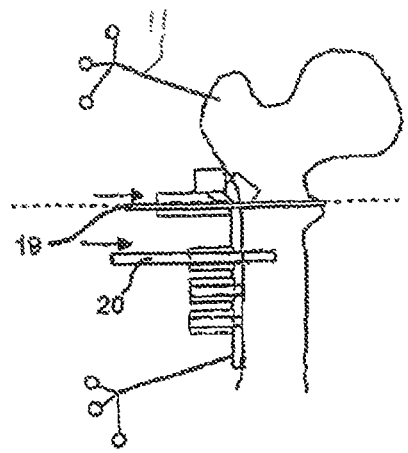
FIG. 3 is a schematic representation of a first aspect of the implant positioning system of the present invention.
Figure 4:
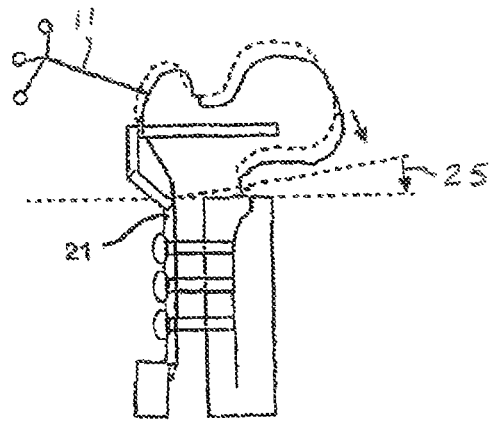
FIG. 4 is a schematic representation of a second aspect of the implant positioning system of the present invention.

After freeing of parts on the bone surface (FIG. 2), the positioning of the reference tracker 11 and the preparation of 2 x-ray recordings of the surgical area from two different directions 12, the following steps are taken: the application of the invention to be described below begins with the placement of the calibrated tracked device 4 flush on the bone surface. Based on the known geometry of the device 4 and its tracked spatial position with respect to the reference tracker 11, the computer-aided control unit of the navigation system can visualize the device in the form of a virtual body 9 in space exactly in the x-ray image 12 with the aid of a corresponding calculation algorithm.

In order for the virtual blade part 10 of the later implant I, which is driven into the bone, now also to be visualized correctly, virtually in the x-ray images 12, the previously planned values of the correction surgery (depending on the complexity of the correction surgery up to 3 rotatory and up to 3 translatory correction values), the size of the wedge angle 16 and the size of the wedge (full wedge or less) as well as the osteotomy plane 17 must be entered into the computer-aided control unit of the navigation system (but can also be entered automatically through the tracked device; it "hangs" on this, virtually). From this, the control unit can calculate the exact spatial position of the blade part 10 in such a way that after removal of the bone wedge and the setting of the implant I, the correction plan is executed accurately.

The particular simplification of the actual surgical execution of the plan by the device 4 consists in the fact that the operator now only has to guide the device 4 flush in the area of the bone surface on which he will attach the implant I later. Thus the operator can shift the device 4 freely on the bone surface 18*a* which helps him as "guide" in order to provide optimal alignment and bone contact of the later implant I and in this process to follow the procedure simultaneously on the screens, such as the shift 18*b* of the plate part 9 and of the blade part 10, which is virtually merged spatially correctly in the x-ray image, and to do this correspondingly to the bone. Thus, for the first time the operator, with the aid of a device 4 tracked directly in the surgical field, can perform the application of the intended correction values directly on the bone for exact planning of the implant I position. In case a medically reasonable implant position cannot be obtained virtually hereby, at this point—without damage to the patient—a modification of the intended correction values can be performed at any time.

After the operator has shifted the device 4 in such a way that an optimum implant I position can be achieved with it, by entering a corresponding command this virtual implant position is stored in the control unit. As an extension of the device 4, however, at this point direct information from the device can also be transferred to the bone. Thus, for example, the correct bone separation plane can be produced directly, for example, by the boring of at least two parallel Kirschner wires 19 or possibly by the creation of bores 20 for the screw channels and thus the surgical procedure can be simplified.

Now, with the aid of the stored data (wedge configuration, plate- and blade position) all further surgical steps can be performed with the commercially-available navigation tools. When these partial steps are carried out exactly, a precise implant seat 21 can be created on the upper thigh bone surface without perforation of the blade part through the lateral hip neck and with optimum contact of the plate part 3 on the femur bone surface.

The method described can be applied with correspondingly modified devices to other cases of application for the planning of implant positions in orthopedics and accident surgery. Hereby planning of structures that lie in the bone (endoprostheses, locking pins, etc.) are also possible.

Figure 5:
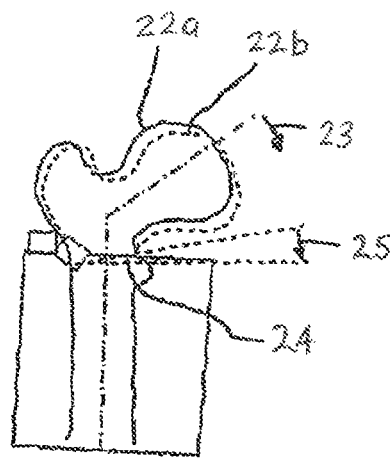
FIGS. 5 and 6 are schematic representations of a prior art surgical implant procedure without the use of the system of the present invention.
Figure 6:
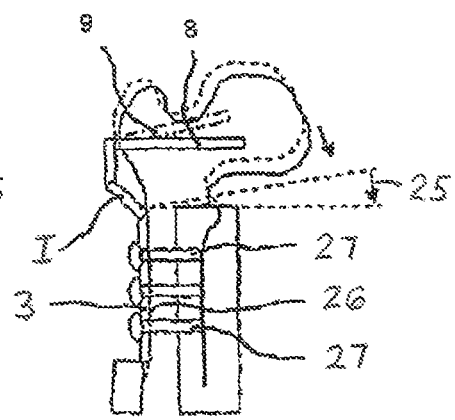

In order to understand the invention better, a description of the medical task with reference to FIGS. 5 and 6 is described.

Description of a bone correction surgery using the example of the femur bone:

For example, if there is a deformity with a tilting of the femur head 22*a* at an angle 23 of 135°, a corrective surgery may become necessary with a reduction of the angle to the normal value of 125°. In order to achieve this, a corresponding 10° wedge 24 which is formed by two saw cuts, is removed and then the femur head 22*a* is tilted downward 25 until the femur head has reached position 22*b*. In order to be able to bind together these two fragments that now sit on top of one another in an unstable manner, usually implants are used which, because of the anatomical conditions, mostly have a special form of a right angle plate I, but other implants can also be used, and the new device 4 described here can be used for that. This plate 3 must lie stably and flush on the bone surface 26 and is attached in this region with screws 27.

However, first the blade part 1 of the plate I must be hammered into the bone fragment near the hip joint. This process is technically extremely demanding, since anatomically the neck of the femur head 22*a*, isthmically shaped, has a considerable narrow spot (analogously to an hourglass) in one plane and the implants used for this frequently take up more than ⅔ of this diameter for reasons of stability. If the operator does not go through this narrow spot accurately, there is a great risk of the danger of bone breakage as well as significant damage to the blood vessels, with severe consequences. Therefore, the bone bed is prepared for later acceptance of the blade part 1 using special blade chisels. Since in this process one must hit the chisel with a hammer, it is understandable that this step in the surgery must be done before the removal of the bone wedge 24, since otherwise the bone fragment near the hip joint would no longer behave sufficiently stably in the surgical field.

However, another significant problem arises hereby for the operator. He must be able to imagine accurately in space how he has to hammer in the blade chisel 28—at this not yet corrected point in time—not at a right angle (90°) to the bone surface 26, but rather, depending on the planned size and orientation of the wedge 24 more steeply, <90° in this example, or in an angle reducing correction, flatter, >90°, has to be the angle 25 in which he inserts it into the bone. The lying of the plate 3 flush against the bone surface 26 and with it the success of the operation depends later, among other things, upon the correctness of this procedure.

However, this process can become significantly more complex than here outlined in an example when it becomes necessary to have five to six degrees of freedom. The exact prediction of the correct chisel blade position 28 will become correspondingly complex.

The invention claimed is:

1. A system for positioning an implant having a first section that is configured to be attached to a first portion of a bone and a section that is configured to be attached to a second portion of the bone, wherein the position of the second portion of the bone is configured to be shifted a planned geometrical shift in relation to the first portion of the bone during an orthopedic procedure, the system comprising:
    a trackable device having a bone contact surface that matches a bone contact surface of the first section of the implant, wherein the device is configured to be located and moved on the accessible bone surface to maximize contact surface with the accessible bone surface; and
    a navigation system configured for tracking the position of the device relative to the position of the bone, the navigation system comprising a computer-aided control unit that is configured to calculate and virtually merge in a spatially correct manner implant parts with image or geometric data of the bone, wherein the calculation is based on navigational data of the trackable device and on data input of planned corrective measures,
    wherein the computer-aided control unit is further configured to, after data input of the planned corrective measures, with the aid of corresponding calculation algorithms and as a function of the position of the device on the accessible bone surface, virtually merge the corresponding position of the second section of the implant with the referenced image or geometric data of the bone, wherein the computer-aided control unit is still further configured to calculate the position of the second section of the implant geometrically offset to take into account a correction equal to the geometry of the planned geometrical shift.

2. The system of claim 1, wherein the bone contact surface is configured to align flush with an accessible bone surface of the first portion of the bone.

3. The system of claim 2, wherein the computer-aided control unit is configured to merge the medically relevant implant parts in the form of three-dimensional geometric bodies and virtually merge the position of the second section of the implant with the position of the bone in a three-dimensional manner.

4. The system of claim 3, wherein the computer-aided control unit is configured to virtually merge the corresponding position of the first section of the implant with the referenced image or geometric data of the bone exactly in the position of the trackable device is in relation to the first portion of the bone.

5. The system of claim 1, wherein the computer-aided control unit is configured to store the position of the trackable device.

6. The system of claim 5, wherein the computer-aided control unit is configured to make available a stepwise manner all planning information for performance of the orthopedic procedure with navigated tools.

7. The system of claim 1, wherein the trackable device includes guide sleeves configured to guide axis-related or plane-related surgical tools, whereby relevant planning information can be transferred directly to the bone using the trackable device.

8. The system of claim 1, wherein the trackable device does not include a portion that matches the geometry of the second section of the implant.

9. A method of planning a position of an incursion into a bone for insertion of an implant having a first section that will be attached to a first portion of a bone and a second section that will be attached to a second portion of the bone, wherein the position of the second portion of the bone will be shifted a planned geometrical shift in relation to the first portion of the bone during an orthopedic procedure, the method comprising the steps:
    tracking the position of a trackable device relative to the bone with a navigation system, wherein the trackable device has a bone contact surface that matches a bone contact surface of the first section of the implant, and wherein the navigation system comprises a camera unit and a computer-assisted control unit that are configured to track the position and orientation of the trackable device with respect to the bone;
    shifting the tracked trackable device on an exposed portion of the bone including the first portion of the bone;
    displaying on a display a virtual position of the first section of the implant on a display of the bone in the position geometrically matching the position of the tracked trackable device on the bone; and
    displaying on the display a virtual position of the second section of the implant geometrically offset to take into account a correction equal to the geometry of the planned geometrical shift.

10. The method of claim 9, further comprising the step:
    saving on the navigation system the position of the trackable device and the virtual position of the second section of the implant when the trackable device is located on accessible bone surface in a position that maximizes contact surface with the accessible bone surface and provides a selected incursion location into the bone.

11. The method of claim 10, further comprising the step of: attaching the first section of the implant onto the first portion of the bone based on the saved position of the trackable device.

12. A system for positioning an implant on a surgically accessible bone surface of a patient, comprising:
    an implant device having a bone contact surface configured to be placed flush against the bone surface of the patient, wherein the bone contact surface of the implant device is geometrically identical to a bone contact surface of the implant;
    a first tracking device attached to the implant device;
    a second tracking device attached to the bone surface; and
    a navigation system that includes a computer assisted control unit connected to a navigation camera,
    wherein the navigation camera is configured to detect the position and orientation of the first and second tracking devices, and wherein the navigation camera is further configured to transmit data describing the position and orientation of the first and second tracking devices to the computer assisted control unit.

13. The system of claim 12, wherein the computer assisted control unit is configured to provide a three dimensional visual simulation displaying the position and orientation of a virtual implant in relation to a virtual bone surface using the data transmitted by the navigation camera so as to allow an operator to determine an optimal alignment of the implant device with the bone surface of the patient, wherein the position and orientation of the virtual implant and the virtual bone surface in the simulation is at least partially determined by the data describing the position and orientation of the first and second tracking devices.

14. The system of claim 13, wherein the control unit is further configured to save the relative positions and orientations of the first and second tracking devices as the operator guides the implant device into optimal alignment such that the simulation may be redisplayed later.

15. The system of claim 12, wherein the implant device includes at least one guiding element configured to guide at least one surgical tool.

16. The system of claim 12, wherein the implant device is rounded at the bone contact surface in order to better correspond to the geometry of the bone surface.

17. The system of claim 15, wherein the at least one surgical tool includes a drilling apparatus that is guided by the guiding elements in the preparation of at least one bore in the bone surface.

18. The system of claim 17, wherein the at least one bore is configured to receive at least one screw that attaches and secures the implant to the bone surface.

19. The system of claim 17, wherein the at least one bore is adapted to receive at least one wire that is configured to guide a saw blade.

20. The system of claim 17, wherein the computer assisted control unit saves the position and orientation of the at least one bore made by the drilling apparatus with respect to the bone surface and the implant device so as to allow the operator to more easily attach the implant to the bone surface.

* * * * *